United States Patent [19]

Clark et al.

[11] 4,163,793

[45] Aug. 7, 1979

[54] USE OF CERTAIN THIOPHENECARBALDEHYDE PHENYLHYDRAZONES AS FUNGICIDES

[75] Inventors: Michael T. Clark, Sittingbourne; Pieter Ten Haken, Herne Bay, both of England

[73] Assignee: Shell Oil Company, Houston, Tex.

[21] Appl. No.: 921,651

[22] Filed: Jul. 3, 1978

Related U.S. Application Data

[63] Continuation-in-part of Ser. No. 838,772, Oct. 3, 1977, abandoned.

[30] Foreign Application Priority Data

Oct. 5, 1976 [GB] United Kingdom ............... 41300/76

[51] Int. Cl.$^2$ ............................................. A01N 9/12
[52] U.S. Cl. ..................................................... 424/275
[58] Field of Search ................ 424/275; 260/332.3 R, 260/332.5

[56] References Cited

U.S. PATENT DOCUMENTS

| | | | |
|---|---|---|---|
| 2,606,166 | 8/1952 | Patrick, Jr. | 260/332.5 |
| 2,841,523 | 7/1958 | Gaertner | 260/332.3 R |
| 3,699,111 | 10/1972 | Kaugars | 424/275 |

*Primary Examiner*—V. D. Turner

[57] ABSTRACT

Certain thiophenecarbaldehyde phenylhydrazones are used to control unwanted fungi.

3 Claims, No Drawings

USE OF CERTAIN THIOPHENECARBALDEHYDE PHENYLHYDRAZONES AS FUNGICIDES

This application is a continuation-in-part of application Ser. No. 838,772, filed on Oct. 3, 1977, now abandoned.

DESCRIPTION OF THE INVENTION

This invention relates to the use of certain phenylhydrazones of certain thiophenecarbaldehydes for the control of fungi. These hydrazones are characterized by the general formula

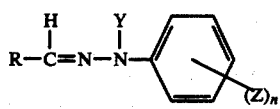

(I)

the particular compounds contemplated in this invention being the following individual species thereof wherein the substituent moieties are as follows (the number(s) preceding the moieties, Z, indicating the position of each of such moieties on the phenyl ring):

| Compound No. | R | Y | n | Z |
|---|---|---|---|---|
| 1 | 2-thienyl | H | 1 | 4-Cl |
| 2 | 2-thienyl | H | 1 | 4-Cl |
| 3 | 2-thienyl | H | 1 | 4-F |
| 4 | 2-thienyl | H | 0 | — |
| 5 | 2-thienyl | H | 1 | 4-methyl |
| 6 | 2-thienyl | —CHO | 0 | — |
| 7 | 5-methyl-2-thienyl | —CHO | 1 | 4-F |
| 8 | 5-methyl-2-thienyl | —CHO | 0 | — |
| 9 | 2-thienyl | H | 1 | 2-Cl |
| 10 | 5-bromo-2-thienyl | H | 0 | — |
| 11 | 2-thienyl | H | 1 | 4-Br |
| 12 | 3-thienyl | —CHO | 0 | — |
| 13 | 3-thienyl | —CHO | 1 | 4-F |
| 14 | 3-thienyl | —CHO | 1 | 4-Cl |
| 15 | 5-bromo-2-thienyl | —CHO | 1 | 4-F |
| 16 | 3-methyl-2-thienyl | —CHO | 0 | — |
| 17 | 5-bromo-2-thienyl | —CHO | 0 | — |
| 18 | 5-chloro-2-thienyl | H | 1 | 4-F |
| 19 | 5-chloro-2-thienyl | —CHO | 1 | 4-F |
| 20 | 5-chloro-2-thienyl | —CHO | 1 | 4-Cl |

The phenylhydrazone fungicides of the invention wherein Y is hydrogen can be prepared by treating a carbonyl compound of the formula: R—CHO, with the appropriate hydrazine of the formula:

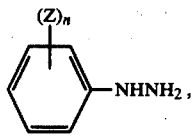

wherein the symbols have the respective meanings already assigned. The hydrazine is used as a salt, preferably the hydrochloride, together with an appropriate base, for example, sodium acetate. The reaction is preferably carried out in a polar solvent at temperatures ranging from ambient temperature to 100° C. Suitable solvents are, for example, ethyl alcohol, diethyl ether or 30% aqueous acetic acid. The reaction may be carried out in the presence or absence of a dehydrative agent.

The phenylhydrazone fungicides of the invention wherein Y represents the formyl moiety can be obtained by treating a compound of the general formula (I), in which Y represents a hydrogen atom, with a formylating agent. Formic acid itself may be used as the formylating agent. However, this reagent was found to give low yields of formylated product, and improved yields of the formulated compound were obtained using the mixed anhydride of formic acid and acetic acid. A preferred formylating agent therefore is one which comprises the mixed anhydride of formic acid and acetic acid, and which may be prepared by mixing appropriate amounts of formic acid and acetic anhydride according to the method of Stevens and van Es (Recueil, 83, 1287–94, (1964)). Alternatively, the acetic/formic anhydride may be prepared by the reaction of acetyl chloride with sodium formate according to the method of Muramatsu et al. (Bull. Chem. Soc. Jap., 38, 244, (1965), or from ketene and formic acid (ibid).

These phenylhydrazones are used in the method of the invention, which consists of, broadly, killing unwanted fungi by subjecting them to the effect of one of those hydrazones. More particularly, the method consists of protecting crops from attack by fungi, in which crops subject to or subjected to such attack, seeds of such crops or soil in which such crops are growing or are to be grown are treated with a fungicidally effective amount of one of the fungicides of the invention. The preferred fungicides are: 2-thiophenecarbaldehyde-p-chlorophenylhydrazone (Compound 1, formula I) and 2-thiophenecarbaldehyde-p-fluorophenylhydrazone (Compound 2).

The fungicides of the invention preferably are used in combination with a carrier. The term "carrier" as used herein means a solid or fluid material, which may be organic or inorganic and of synthetic or natural origin, with which the fungicide is mixed or formulated to facilitate its application to the plant, seed, soil or other object to be treated, or its storage, transport or handling. The carrier may be a solid or a fluid. Any of the materials usually applied in formulating pesticides may be used as the carrier.

Suitable solid carriers are natural and synthetic clays and silicates, for example natural silicas such as diatomacious earths; magnesium silicates, for example, talcs; magnesium aluminum silicates, for example, attapulgites and vermiculites; aluminum silicates, for example, kaolinites, montmorillinites and micas; calcium carbonates; calcium sulphate; synthetic hydrated silicon oxides and synthetic calcium or aluminum silicates; elements such as for example, carbon and sulphur; natural and synthetic resins such as, for example coumarone resins, polyvinyl chloride and styrene polymers and copolymers; solid polychlorophenols; bitumen; waxes such as for example, beeswax, paraffin wax, and chlorinated mineral waxes; and solid fertilizers, for example superphosphates.

Examples of suitable fluid carriers are water, alcohols, such as for example, isopropanol; glycols; ketones such as for example, acetone, methyl ethyl ketone, methyl isobutyl ketone and cyclohexanone; ehters; aromatic hydrocarbons such as for example, benzene, toluene and xylene; petroleum fractions such as for example, kerosine; light mineral oils; chlorinated hydrocarbons, such as for example, carbon tetrachloride, perchloroethylene, trichloroethane, including liquified normally vaporous gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides, fungicides, or insecticides may be used. Examples of suitable surface-active agents are the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example, sodium lauryl sulphate, sodium secondary alkyl sulphates, sodium salts of sulphonated caster oil, and sodium alkylaryl sulphonates such as sodium dodecylbenzene sulphonate; and polymers of ethylene oxide and copolymers of ethylene oxide and propylene oxide.

The fungicides of the invention may be formulated as wettable powders, dusts, granules, solutions, emulsifiable concentrates, emulsions, suspension concentrates and aerosols and will generally contain 0.5 to 95% w, preferably 0.5 to 75% w, of the fungicide. Wettable powders are usually compounded to contain 25, 50 or 75% w of the fungicide and usually contain, in addition to solid carrier, 3–10% w of a dispersing agent and, where necessary, 0–10% w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of the fungicide. Granules are usually prepared to have a size between 10 and 100 BS mesh (1.676–0.152 mm), and may be manufactured by agglomeration or impregnation techniques. Generally, granules will contain ½–25% w toxicant and 0–10% w of additives such as stabilizers, slow release modifiers and binding agents. Emulsifiable concentrates usually contain, in addition to the solvent and, when necessary, co-solvent, 10–50% w/v toxicant, 2–20% w/v emulsifiers and 0–20% w of appropriate additives such as stabilizers, penetrants and corrosion inhibitors. Suspension concentrates are compounded so as to obtain a stable, non-sedimenting, flowable product and usually contain 10–75% w of the fungicide, 0.5–15% w of dispersing agents, 0.1–10% w of suspending agents such as protective colloids and thixotropic agents, 0–10% w of appropriate additives such as defoamers, corrosion inhibitors, stabilizers, penetrants and stickers, and as carrier, water or an organic liquid in which the toxicant is substantially insoluble; dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick "mayonnaise"-like consistency.

The formulations may also contain other ingredients, for example, other compounds possessing pesticidal, such as insecticidal, herbicidal or acaricidal, properties.

The invention is further illustrated in the following Examples. In each case, the identity of the product was confirmed by appropriate chemical and spectral analyses.

EXAMPLE 1

Preparation of 2-thiophenecarbaldehyde-p-chlorophenylhydrazone (1)

14.8 g of 2-thiophenecarbaldehyde was added to a mixture of 25.2 g of p-chlorophenylhydrazine hydrochloride and 33.6 g of sodium acetate in 400 ml of 50% aqueous ethyl alcohol. The mixture was heated on a water bath for 30 minutes. After cooling, the precipitated solid was collected and crystallized from ethyl alcohol to give 1, as yellow needles, mp 137° C.

EXAMPLE 2

Preparation of 2-thiophenecarbaldehyde-N-formyl-p-chlorophenylhydrazone (2)

5.29 g of 1 was dissolved in 25 ml of 1,2-dimethoxyethane. The solution was treated with 5.4 g of the mixed anhydrides of formic acid and acetic acid, prepared by mixing the appropriate amounts of formic acid and acetic anhydride, and distilling the product. The resulting mixture was held overnight at room temperature. The solvent was evaporated and the residue was extracted with chloroform. The extract was washed with sodium bicarbonate solution, dried and the solvent evaporated. The residue was treated with charcoal in hexane; the mixture was filtered and the filtrate let stand. 2 crystallized out, mp 103°–105° C.

EXAMPLE 3

Preparation of 2-thiophenecarbaldehyde-p-fluorophenylhydrazone (3)

1.6 g of p-fluorophenylhydrazine hydrochloride and 4.9 g of anhydrous sodium acetate were dissolved in 300 ml of 50% aqueous ethyl alcohol, and the mixture was filtered to remove sodium chloride. 1.1 g of 2-thiophenecarbaldehyde in 3 ml of ethyl alcohol was then added to the filtrate and the mixture was refluxed for 30 minutes. After cooling, the precipitate was collected and crystallized from ethyl alcohol to give 3, as pale yellow plates, mp 138°–140° C.

Table I identifies and set out the melting points of further individual species of the fungicides of the invention, which were prepared by the procedures illustrated in Examples 1–3.

Table I

| Compound No. | Melting Point (°C.) |
|---|---|
| 4 | 134–135 |
| 5 | 137 |
| 6 | 125–127 |
| 7 | 134–136 |
| 8 | 110–112 |
| 9 | 90–92 |
| 10 | 111–114 |
| 11 | 134–138 |
| 12 | 103–105 |
| 13 | 107.5–110 |
| 14 | 118–120.5 |
| 15 | 107–110 |
| 16 | 127–128 |

Table I-continued

| Compound No. | Melting Point (°C.) |
|---|---|
| 17 | 123–124 |
| 18 | 107–110 |
| 19 | 121–123 |
| 20 | 145–146 |

Fungicidal activity of these phenylhydrazones was established as follows:

Activity against vine downy mildew (*Plasmopara viticola*)

The test was a direct antisporulant one using a foliar spray. The lower surfaces of leaves of whole vine plants, were inoculated by spraying with an aqueous suspension containing $10^5$ zoosporangia per milliliter 4 days prior to treatment with the test compound. The inoculated plants were kept for 24 hours in a high humidity compartment, 48 hours at glasshouse ambient temperature and humidity and then were returned for further 24 hours to high humidity.

The plants then were dried and the infected leaves detached and sprayed on the lower surfaces at a dosage of 1 kilogram of the test compound per hectare using a track sprayer. After drying, the petioles of the sprayed leaves were dipped in water and the leaves returned to high humidity for a further 72 hours incubation, followed by assessment. Assessment was based on the percentage of the leaf area covered by sporulation compared with that on control leaves.

Activity against barley powdery mildew (*Erysiphe graminis*)

The test measured the direct antiporulant activity of the test compounds, applied as a foliar spray. For each compound about 40 barley seedlings were grown to the one-leaf stage in a plastic pot of sterile potting compost. Inoculation was effected by dusting the leaves with conidia of Erysiphe graminis. 24 hours after inoculation the seedlings were sprayed with a solution of the test compound in a mixture of acetone (50%) surfactant (0.04%) and water using a track sprayer. The rate of application was equivalent to 1 kilogram of active material per hectare. First assessment of disease was made 5 days after treatment, when the overall level of sporulation on treated posts were compared with that on control pots.

Activity against wheat brown rust (*Puccinia recondita*)

The test was a direct antisporulant one using a foliar spray. Pots containing about 25 wheat seedlings per pot, at first leaf stage, were inoculated by spraying the leaves with an aqueous suspension containing $10^5$ spores per milliliter plus a little Triton X-155, 20–24 hours before treatment with the compound under test. The inoculated plants were kept overnight in a high humidity compartment, dried at glasshouse ambient temperature, and then sprayed at a dosage of 1 kilogram of active material per hectare using a track sprayer. After treatment the plants were kept at glass-house ambient temperature and assessment made 11 days after treatment. Assessment was based on the relative density of sporulating pustules per plant compared with that on control plants.

Activity against broad bean rust (*Uromyces fabae*)

The test was a translaminar antisporulant one using foliar spray. Pots containing 1 plant per pot were inoculated by spraying an aqueous suspension, containing $5 \times 10^4$ spores per milliliter plus a little Triton X-155, onto the undersurface of each leaf 20–24 hours before treatment with the test compound. The inoculated plants were kept overnight in a high humidity compartment, dried at glass-house ambient temperature and then sprayed, on the leaf upper surfaces, at a dosage of 1 kilogram per hectare of active material using a track sprayer. After treatment the plants were kept at glasshouse temperature and assessment made 11 days after treatment. Symptoms were assessed on the relative density of sporulation per plant compared with that on control plants.

The extent of disease control is set out in Table II and expressed as a control rating according to the criteria:
0 = less than 50% disease control
1 = 50–80% disease control
2 = greater than 80% disease control Table II

| Compound No. | Fungicidal Activity | | | |
|---|---|---|---|---|
| | Pr.a. | E.g. | P.r. | U.f. |
| 1 | 2 | 0 | 0 | 0 |
| 2 | 0 | 0 | 0 | 2 |
| 3 | 2 | 1 | 2 | 2 |
| 4 | 2 | 0 | 1 | 2 |
| 5 | 2 | 0 | 0 | 0 |
| 6 | 0 | 0 | 0 | 2 |
| 7 | 0 | 0 | 0 | 2 |
| 8 | 0 | 0 | 0 | 2 |
| 9 | 0 | 0 | 0 | 2 |
| 10 | 2 | 0 | 0 | 0 |
| 11 | 2 | 0 | 0 | 0 |
| 12 | 0 | 0 | 0 | 2 |
| 13 | 1 | 0 | 0 | 2 |
| 14 | 2 | 0 | 0 | 0 |
| 15 | 2 | 0 | 0 | 0 |
| 16 | 1 | 0 | 0 | 2 |
| 17 | 0 | 0 | 0 | 2 |
| 18 | 2 | 1 | 0 | 0 |
| 19 | 0 | 0 | 0 | 2 |
| 20 | 0 | 1 | 2 | 0 |

We claim:

1. A method for killing unwanted fungi which comprises subjecting such fungi to the effect of one of twenty hydrazones of the formula:

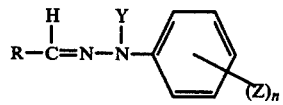

(I)

the twenty being the individual species wherein the substituent moieties are as follows, the numbers preceding the moieties, Z, indicating the position of each of such moieties on the phenyl ring:

| R | Y | n | Z |
|---|---|---|---|
| 2-thienyl | H | 1 | 4-Cl |
| 2-thienyl | H | 1 | 4-Cl |
| 2-thienyl | H | 1 | 4-F |
| 2-thienyl | H | 0 | — |
| 2-thienyl | H | 1 | 4-methyl |
| 2-thienyl | —CHO | 0 | — |
| 5-methyl-2-thienyl | —CHO | 1 | 4-F |
| 5-methyl-2-thienyl | —CHO | 0 | — |

-continued

| R | Y | n | Z |
| --- | --- | --- | --- |
| 2-thienyl | H | 1 | 2-Cl |
| 5-bromo-2-thienyl | H | 0 | — |
| 2-thienyl | H | 1 | 4-Br |
| 3-thienyl | —CHO | 0 | — |
| 3-thienyl | —CHO | 1 | 4-F |
| 3-thienyl | —CHO | 1 | 4-Cl |
| 5-bromo-2-thienyl | —CHO | 1 | 4-F |
| 3-methyl-2-thienyl | —CHO | 0 | — |
| 5-bromo-2-thienyl | —CHO | 0 | — |
| 5-chloro-2-thienyl | H | 1 | 4-F |
| 5-chloro-2-thienyl | —CHO | 1 | 4-F |
| 5-chloro-2-thienyl | —CHO | 1 | 4-Cl |

2. A method according to claim 1 wherein the hydrazone is 2-thiophenecarbaldehyde-p-chlorophenylhydrazone.

3. A method according to claim 1 wherein the hydrazone is 2-thiophenecarbaldehyde-p-fluorophenylhydrazone.

* * * * *